United States Patent [19]
Bonnet

[11] Patent Number: 4,606,330
[45] Date of Patent: Aug. 19, 1986

[54] DEVICE FOR DISINTEGRATING STONES IN BODILY CAVITIES OR DUCTS

[75] Inventor: Ludwig Bonnet, Knittlingen, Fed. Rep. of Germany

[73] Assignee: Richard Wolf GmbH, Fed. Rep. of Germany

[21] Appl. No.: 632,302

[22] Filed: Jul. 19, 1984

[30] Foreign Application Priority Data

Aug. 9, 1983 [DE] Fed. Rep. of Germany ... 8322900[U]

[51] Int. Cl.⁴ ............................................. A61B 1/00
[52] U.S. Cl. ................................. 128/7; 128/303.15; 128/328
[58] Field of Search ................... 128/4, 5, 6, 7, 8, 660, 128/303.15, 328

[56] References Cited

U.S. PATENT DOCUMENTS

| | | | |
|---|---|---|---|
| 3,782,369 | 1/1974 | Storz | 128/7 |
| 3,835,842 | 9/1974 | Iglesias | 128/7 |
| 3,850,162 | 11/1974 | Iglesias | 128/6 |
| 3,886,933 | 6/1975 | Mori et al. | 128/7 |
| 3,889,656 | 6/1975 | Krawitt | 128/7 |
| 4,078,555 | 3/1978 | Takahashi | 128/4 |
| 4,132,227 | 1/1979 | Ibe | 128/7 |
| 4,137,920 | 2/1979 | Bonnet | 128/7 |
| 4,178,920 | 12/1979 | Cawood, Jr. et al. | 128/4 |
| 4,196,736 | 4/1980 | Watanabe | 128/7 |
| 4,327,711 | 5/1982 | Takagi | 128/4 |
| 4,372,295 | 2/1983 | Heckele | 128/4 |
| 4,392,485 | 7/1983 | Hiltebrandt | 128/6 |

*Primary Examiner*—Andrew H. Metz
*Assistant Examiner*—Anthony McFarlane
*Attorney, Agent, or Firm*—Hill, Van Santen, Steadman & Simpson

[57] ABSTRACT

A device for shattering stones in bodily cavities or ducts; incorporating an endoscope. A passage for auxiliary instruments and for flushing of a bodily cavity extends through the shaft of the endoscope. A casing section at one end of the endoscope comprising a light connector stub and an angled eyepiece element. The casing section may have coupled to it an insertion element comprising two closable passages, of which one is for passing a stone disintegrator instrument and the other is for passing a flexible probe locating the stone. Both said passages communicate with the adjacent end of a cross-sectionally substantially oval passage through the shaft.

7 Claims, 3 Drawing Figures

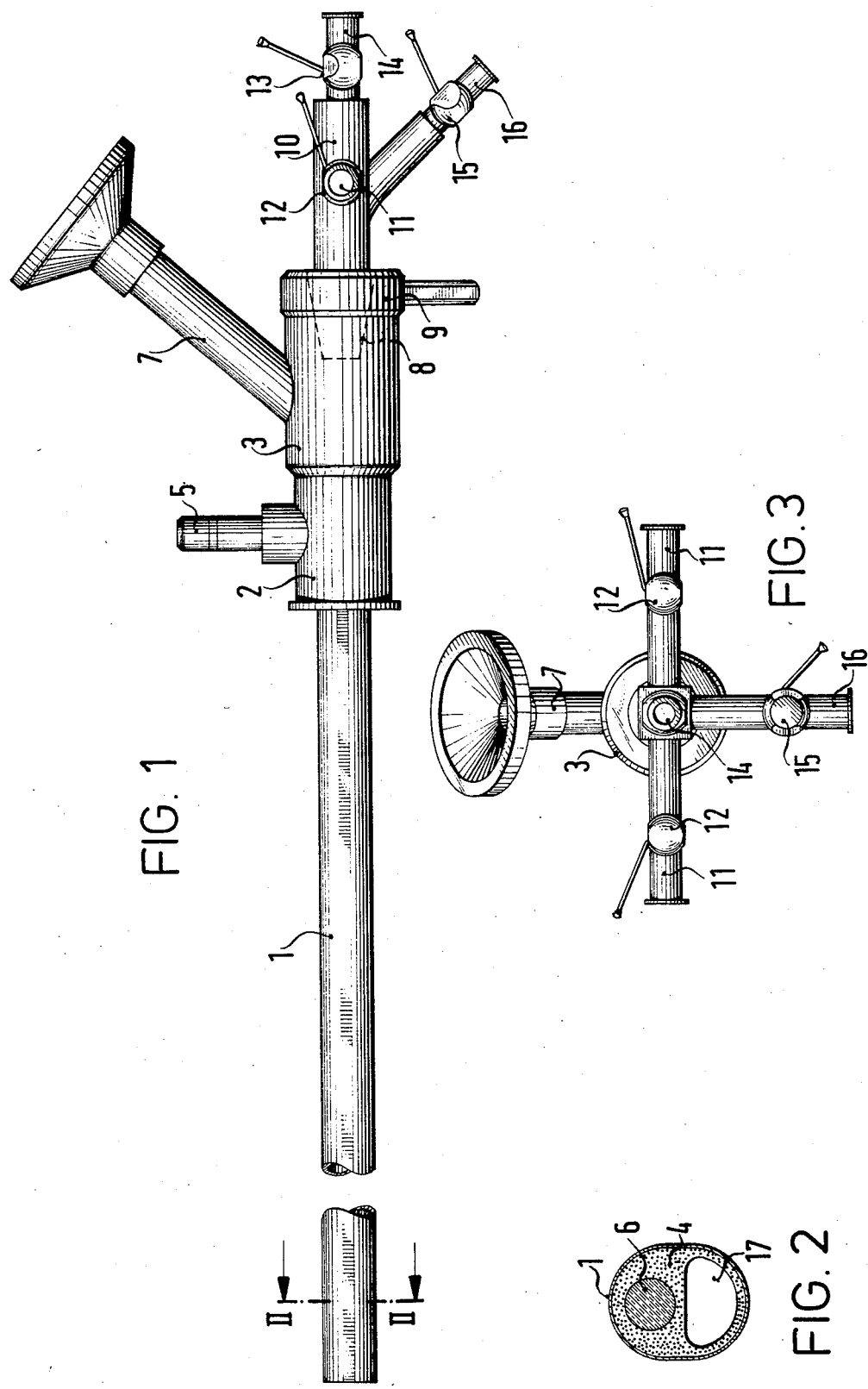

DEVICE FOR DISINTEGRATING STONES IN BODILY CAVITIES OR DUCTS

BACKGROUND OF THE INVENTION

1. Field of the Invention

The invention relates to a device for disintegrating stones in bodily cavities or ducts, in particular ureter stones, comprising an endoscope with a shaft which has extending through it a passage for traversal by auxiliary instruments and for flushing a bodily cavity, and having a rear casing section attached to the shaft with a light connector stub and an angled eyepiece element.

2. Description of the Prior Art

The utilisation of atraumatic ultrasonic probes which require a simultaneous check by means of an X-ray apparatus without direct visual supervision, is known for the lithotripsy of ureter stones.

Known electrohydraulically applicable probes may lead to injuries of the mucous membrane of the ureter because of the uncontrollable explosion-like stone disintegration, or stone residues caused by repeated stone growth may get back into the kidney.

SUMMARY OF THE INVENTION

It is an object of the invention to provide a device which can be used for locating and destroying stones in bodily cavities or ducts, without the risk of damage being caused by shattered stone fragments.

The present invention provides a device for shattering stones in bodily cavities or ducts comprising an endoscope having a shaft through which extends a passage for insertion therethrough of auxiliary instruments and for flushing fluid, a casing section attached to one end of the shaft, a light connector stub and an angled eyepiece element, the casing also having coupled to it an insertion element having a first closable passage for an instrument for disintegrating stones and a second closable passage for a flexible probe for detecting the stone, both closable passages leading into the casing and hence into the passage of the shaft.

Using the device of the invention, at least in preferred embodiments, it is possible to locate a stone in a long, thin fluid-draining duct, such as the ureter, under constant visual verification and to shatter the same by means of an ultrasonic probe, at the same time precluding the possibility, which can arise using an electrohydraulic probe, of individual stone particles resulting from the explosion-like stone disintegration being able to get back into the kidney.

More specifically, it is possible for a probe for locating the stone, for example a "Dormia" cage or a balloon catheter, to be inserted under observation into the ureter through the insertion element and the shaft of the endoscope, and to hold the stone fast by means of the cage or to establish the position of the stone by inflation of the balloon behind the stone, so that the stone is subsequently caused to break up by means of the stone-disintegrator probe, for example by ultrasonic vibration or by electrohydraulic means, whereupon the stone parts may be removed via the passage of the endoscope and flushing passages of the insertion element.

BRIEF DESCRIPTION OF THE DRAWINGS

FIG. 1 shows a side view of an endoscope comprising an insertion element, in accordance with the invention, FIG. 2 shows a cross-section along the line II—II of FIG. 1, and FIG. 3 shows a rear end view of the endoscope with its insertion element, see in distal direction.

DETAILED DESCRIPTION OF PREFERRED EMBODIMENTS

The endoscope shown in the drawings has a cross-sectionally oval shaft 1 for insertion into a bodily cavity with a casing section 2 attached to its rear end, the casing having a stepped enlargement 3. The shaft 1 has extending through it a fibre optic guide 4 to which light is fed from a projector via a stub 5, and an optical observation system 6 having an angled eyepiece element 7. The casing section 3 contains a conical recess 8 known per se and a bayonet catch 9 for an exchangeable guiding element 10 having a coupling cone which can be tightly inserted into the cone seat 8 and locked.

The guiding element 10 is equipped with two flushing connectors 11 closable by means of cocks 12 and has a passage 14 extending parallel to the longitudinal axis and closable by means of a cock 13, which is intended to be traversed by a disintegrator probe, for example an ultrasonic lithriptor, and a second passage 16 of smaller cross-section which is set at an oblique angle to the axis and closable by means of a cock 15 intended to be traversed by probes for securing or immobilising a stone in the ureter or in thin elongate bodily cavities. The probe may for example be a flexible "Dormia" cage or balloon catheter.

The passages 14 and 16 extend parallel and advantageously separately side-by-side to the conical end of the insertion element 10, and both open into a wide substantially oval passage 17 extending parallel to the optical observation system 6 through the shaft 1. Using the insertion element 10 and the extension of its passage, the two probes which are to be passed through the endoscope passage 17 are guided parallel and twisting of the flexible probes is prevented thereby.

By means of the coupling 8,9 the insertion element 10 may be turned at will to place the probe passage 16 in a particular position, for example. It is also possible to exchange the element 10 for another element with a different arrangement of passages.

The procedure followed when utilising the device described above is as follows: The rigid shaft 1 is inserted via the urethra and the bladder into the ureter. A probe for location of the diagnosed stone is then inserted via the passage 16 and the shaft 1, and it is possible with optical monitoring to move the probe past between the ureter and the stone at an appropriate point and then to surround the stone by means of the cage or to inflate the balloon of a balloon catheter behind the stone. Having thus immobilised the stone, the disintegrator probe is led to the stone through the passage 14 and the shaft 1 and the shattering of the stone is then undertaken. The stone fragments may finally be removed via the flushing passages 11.

I claim:

1. A device for shattering stones in bodily cavities or ducts, comprising:
    an endoscope having a shaft attached to an enlarged axial proximal end casing section, said shaft having an axial channel therein for the passage of instruments and of flushing fluid, and being provided with permanent optical guide means, said channel open to the axial proximal end of said casing;

a light connector stub and an eyepiece provided on said casing and are further fixed to said casing and connected to said optical guide means, said eyepiece projecting at an angle from said casing;

an insertion element removably connected to said casing, said element having a proximal end;

a first closable passage in said insertion element extending axially thereof and opened to the proximal end thereof, communicating with said channel for insertion of an instrument for shattering stones; and a second closable passage in said insertion element, communicating with said channel for insertion of a flexible probe for detecting stones;

independent means for closing the first and second passages, said first and second passages communicating to said channel.

2. A device as claimed in claim 1 further comprising feed and drain ducts through said insertion element, communicating with said closable passages for the passage of flushing fluid thereto and hence to said channel.

3. A device as claimed in claim 1 wherein said first passage passes axially straight through said insertion element and said second passage is of smaller cross-section than the first and issues obliquely from the side of the insertion element, and wherein said first and second passages extend parallel to and separate from one another through said casing to said channel, adjacent to said optical guide means.

4. An insertion element for inserting stone-detecting and disintegrating means into an axial channel of an endoscope said insertion element comprising:

a body portion having coupling means for coupling the element to said endoscope;

a first closable passage through said body portion, communicating with said coupling means for insertion of said stone-disintegrating means and a second closable passage through said body portion communicating with said coupling means for insertion of a probe for detecting stones.

5. A device for locating and shattering stones in bodily cavities or ducts, comprising:

an endoscope having an elongated shaft and an enlarged portion at one end of said shaft;

a fibre optic guide extending through said shaft;

a light connector stub on said enlarged portion, connected to said fibre optic guide;

an optical observation system extending through said shaft;

an eyepiece extending obliquely from said enlarged portion and fixed thereto and carried thereby and connected to said optical observation system;

an axial channel through said shaft and said enlarged portion;

an insertion element axially removably coupled to said enlarged portion of the endoscope having a proximal end;

a first closable passage extending axially through said insertion element and open to a proximal end of said insertion element and communicating with said channel for straight, axial insertion of stone disintegrating means;

a second closable passage having a proximal end, said second passage having a portion thereof, extending through said insertion element parallel to and separately from said first closable passage, and communicating with said axial channel for insertion of a flexible probe for detecting stones, said second passage proximal end being directed at an angle to an axis of the insertion element, said insertion element having an axis; and closable feed and drain ducts for flushing fluid, leading into said closable passages.

6. A method of locating and disintegrating stones in a bodily cavity or duct which comprises the steps of:

inserting into said cavity or duct an elongated shaft of an endoscope having an axial channel therethrough;

coupling an insertion element to an enlarged end of endoscope inserting through a closable passage in said insertion element and the axial channel, a flexible probe to locate and entrap a stone in said cavity or duct;

inserting through another closable passage in said insertion element and through the axial channel an ultrasonic probe for disintegrating the entrapped stone;

energising said probe to disintegrate the stone and flushing out the fragments of the disintegrated stone with flushing fluid fed through said closable passages.

7. A device for visually locating and shattering stones in bodily cavities or ducts which comprises a sheath assembly for insertion into the body, the sheath assembly having elongated shaft with distal end and proximal end, optical means received in said shaft including fiber optic light carrying means and an optical observation system, eyepiece means projecting from said sheath assembly adjacent its proximal end at an angle to an axis of the sheath assembly, an instrument channel extending through said shaft from said distal end to said proximal end, an insertion element removably coupled to said sheath assembly, first and second passages through said insertion element, said insertion element having distal end and proximal end, said distal end of said insertion assembly communicating with said instrument channel of said shaft, said first and second passages having independent means for closing said passages, said first passage having a proximal end, said first passage aligned parallel with the axis of said sheath assembly and said proximal end of said first passage open axially whereby an instrument for shattering stones can be inserted linearly axially through said first passage, said insertion element, said sheath assembly and said channel, said second passage having portions extending through said insertion element parallel to portions of said first passage and communicating with said instrument channel, said second passage having a proximal end extending at an obtuse angle to the axis of said sheath assembly.

* * * * *